(12) United States Patent
Sykes (10) Patent No.: US 7,950,290 B2
(45) Date of Patent: *May 31, 2011

(54) APPARATUS AND METHOD FOR DETERMINING FAILURE MODE IN A SHEAR OR PULL TEST DEVICE

(75) Inventor: Robert John Sykes, Essex (GB)

(73) Assignee: Nordson Corporation, Westlake, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 12/778,427

(22) Filed: May 12, 2010

(65) Prior Publication Data

US 2010/0218615 A1 Sep. 2, 2010

Related U.S. Application Data

(63) Continuation of application No. 12/280,235, filed as application No. PCT/GB2007/000825 on Mar. 8, 2007, now Pat. No. 7,748,278.

(30) Foreign Application Priority Data

Mar. 8, 2006 (GB) .................................. 0604700.5

(51) Int. Cl.
*G01N 3/08* (2006.01)
(52) U.S. Cl. ............................................ 73/827; 73/760
(58) Field of Classification Search ............. 73/760–827
See application file for complete search history.

(56) References Cited

U.S. PATENT DOCUMENTS 3,577,775 A * 5/1971 Henderson ..................... 73/827
4,417,478 A 11/1983 Jon et al.
6,164,514 A 12/2000 Miller
6,341,530 B1 1/2002 Sykes
6,371,355 B1 4/2002 Newman (Continued)

FOREIGN PATENT DOCUMENTS

WO 2005/114722 A1 12/2005

OTHER PUBLICATIONS

European Patent Office, International Search Report in PCT Application Serial No. PCT/GB2007/000825, May 22, 2007.

(Continued)

*Primary Examiner* — Max Noori
(74) *Attorney, Agent, or Firm* — Wood, Herron & Evans, L.L.P.

(57) ABSTRACT

A method and apparatus for determining a mode of failure of a bond between an electrically conductive ball deposit and a substrate when breaking the ball deposit off of the substrate. The method and apparatus utilize tool force and displacement values to plot a force/displacement curve. The force/displacement curve is used to calculate the energy necessary to break the ball deposit off of the substrate. The energy value of a portion of a force/displacement curve is selected by reference to a peak force. In one preferred embodiment, this energy value is compared with a predetermined reference energy value to indicate a mode of failure. The peak force is preferably the maximum peak force, in the preferred embodiment, the method and apparatus distinguish between a ductile failure mode and a brittle failure mode.

14 Claims, 4 Drawing Sheets

U.S. PATENT DOCUMENTS

| | | | |
|---|---|---|---|
| 6,564,115 | B1 | 5/2003 | Kinnaird |
| 7,730,790 | B2 * | 6/2010 | Sykes ............................ 73/842 |
| 2002/0187866 | A1 | 12/2002 | Touhey et al. |
| 2005/0109117 | A1 | 5/2005 | Jian et al. |
| 2008/0257059 | A1 * | 10/2008 | Peecock et al. ................ 73/827 |
| 2008/0314159 | A1 | 12/2008 | Sykes |
| 2009/0056469 | A1 * | 3/2009 | Sykes ............................ 73/827 |
| 2009/0301216 | A1 | 12/2009 | Sykes |

OTHER PUBLICATIONS

Robert Erich et al., Shear Testing and Failure Mode Analysis for Evaluation of BGA Ball Attachment, Electronics Manufacturing Technology Symposium, 1999, pp. 16-22.

Robert Sykes, Crashtest fur Ball-to-Pad, Productronic, No. 11, 2005, pp. 2-4.

* cited by examiner

APPARATUS AND METHOD FOR DETERMINING FAILURE MODE IN A SHEAR OR PULL TEST DEVICE

CROSS-REFERENCE TO RELATED APPLICATIONS

This application is a continuation of application Ser. No. 12/280,235, filed Aug. 21, 2008 (pending), which is a U.S. National Phase of PCT Application Serial No. PCT/GB2007/000825, filed Mar. 8, 2007 (expired). The entire disclosure of each of these prior related applications is hereby incorporated by reference herein.

BACKGROUND

This invention concerns apparatus and methods for testing the strength of a bond in a semi-conductor device, and more particularly the strength of a bond between a substrate and a means of electrical connection thereto, typically a part-spherical deposit. Such deposits can be of solder, gold or other materials and are sometimes referred to as solder bumps or ball grid arrays.

Semiconductor devices are very small, typically from 0.2 mm square to 25 mm square. These devices have sites for the bonding of electrical conductors thereto. Sites typically comprise part spherical electrically conductive deposits of for example gold or solder, collectively known as balls, which in use have the appearance of a squashed sphere or low circular dome, and a diameter in the range 50-1000 µm. These deposits form part of the electrical path between, for example, a printed circuit board and a chip, and may directly connect components, or may be joined to a conductor which is itself connected to another component. Many such balls may be provided as a regular grid-like array on a substrate.

Discrete balls are typically applied to a substrate and reflowed during subsequent connection to another component.

It is necessary to test the mechanical strength of the bond between the ball deposit and the substrate in order to give confidence that the production bonding method is adequate, and that the bond strength is sufficient. One kind of test applies a shear load to the ball deposit by means of a shear tool of a shear test machine in which the substrate is secured. Another kind of test applies a pulling load to the ball deposit by means of a gripper of a pull test machine to which the substrate is secured.

There are two principal types of failure modes which occur during these types of test: ductile failure mode and brittle failure mode. Breaking a strong bond will result in ductile failure mode of the ball deposit, with progressive deformation of the ball deposit until the ball deposit is broken with part of the ball deposit often remaining adhered to the substrate. Breaking a weak bond will typically result in brittle failure mode with the ball deposit more or less cleanly tearing away from the substrate, leaving little residue adhered thereto. Consequently, inspection of the substrate after such a test can often indicate the mode of failure. It would be advantageous to provide test machine users with a test machine which could monitor parameters of the test tool and process those parameters to indicate automatically to the user the nature of the failure mode, and particularly whether a ductile or brittle failure mode. These "principle" failure modes can be subdivided into many other classifications. For example a brittle fracture can occur at the bond between the ball deposit and the conductive pad it is adhered to or between the conductive pad and the substrate that it is mounted to.

A known shear test apparatus comprises a machine having a support surface and a test head movable in a controlled manner relative to the support surface. The test head carries a cartridge specific to the test to be performed and having one of several interchangeable shear tools thereon. Typically the shear tool will be sized and/or shaped to suit the ball deposit to be tested. In use, the substrate to be tested is attached to the support surface of the machine, and the tool is mounted into the cartridge and driven against the ball deposit to perform the required test, which may be for example a shear test or a reciprocating fatigue test. Typically the tool moves against a stationary deposit.

A known pull test machine is similar and carries a cartridge having a gripper adapted to the size and shape of the ball deposit to be tested and operable to exert a pulling load on the ball deposit substantially orthogonally to the substrate.

Although shear tests and pull tests are somewhat different, the force/displacement characteristics are similar and can be used to classify the failure mode, particularly whether the failure mode is ductile or brittle.

A typical tool is small. The cartridge upon which the tool is secured has a flexible element on which is mounted one or more force gauges (such as strain gauges). Thus, the force between the tool and ball deposit is measured at a distance by deflection in the flexible elements of the cartridge. WO-A-2005/114722 shows an example of such a cartridge. The cartridge shown in WO-A-2005/114722 can be used in the Dage Model 4000 Series machine available from Dage Precision Industries Ltd., of Aylesbury, United Kingdom. This machine typically measures the peak force necessary to break a ball deposit off a substrate. Although the machine is able to measure peak force, it is difficult to determine whether the bond between the ball and substrate has failed as a result of ductile failure mode or brittle failure mode based on measurement of peak force alone. This difficulty arises from the fact that the peak forces in both brittle and ductile failure modes may be broadly similar for a given size and shape of ball deposit.

It would be desirable to provide a method and apparatus for distinguishing the mode of bond failure, and particularly to distinguish between the brittle and ductile failure modes and any other modes that these principle modes are subdivided into. As mentioned above, if breaking a ball off a substrate produces a ductile failure mode, that indicates that the bond between the ball and the substrate is a good bond, whereas a brittle failure mode would indicate that the bond is suspect and may be poor. Thus, providing the user of the machine with an output displayed on the machine monitor, for example, which indicates to the user whether the failure mode was ductile or brittle, indicates to the user whether the bond tested was a good bond or a poor bond.

SUMMARY

According to a first aspect of the invention there is provided a method of determining the mode of bond failure when an electrically conductive ball deposit bonded to a substrate is subjected to a force to break the ball deposit off of the substrate, the method comprising the steps of:

utilizing a tool of a bond testing machine to break the ball deposit off of the substrate, measuring the force applied by the tool to the ball deposit while the tool is breaking the ball deposit off of the substrate, measuring the displacement of the tool relative to the bond substrate while the tool is breaking the ball deposit off of the substrate, determining a selected peak force applied by the tool to the ball deposit, utilizing the force and displacement measurements to determine the associated value of energy absorbed by the ball deposit from the tool, the energy being determined with reference to said selected peak applied force, and comparing said associated value of energy to a reference value of energy to indicate a mode of failure.

The method permits the mode of failure to be determined which has not been possible with prior art methods. The tool may be a shear tool for applying a shear force to the ball deposit, or a gripper for applying an orthogonal pull force to the ball deposit.

In determining the energy absorbed by reference to the peak applied force, the value of energy absorbed before said selected peak applied force and/or the value of energy absorbed after said selected peak applied force may be used as said associated value in the comparison step.

In a preferred embodiment, the value of energy absorbed after said selected peak applied force is used as said associated value, and is compared with a reference value to determine one of two failure modes, where one failure mode corresponds to an energy value below said reference value, and the other failure mode corresponds to an energy value above said reference value.

The selected peak applied force may be the sole peak applied force. The method may include the further step of determining which of a plurality of peaks of applied force is selected as said selected peak applied force.

In this refinement the selected peak applied force may not be the maximum peak applied force, but a preceding or succeeding peak which better permits a mode of failure to be distinguished.

The method may further include the step of determining whether one of a plurality of peaks of applied force should be discarded for the purpose of determining said selected peak applied force.

Such a method permits the effect of transient or very small peaks to be eliminated. One method of distinguishing such peaks is to provide a filter adapted to eliminate peaks of less than a predetermined significance, for example to eliminate peaks for which the next succeeding minimum has a value greater than a given percentage of the value of that peak, typically greater than 90%.

According to a second aspect of the invention there is provided apparatus for applying a load to an electrically conductive ball deposit on a substrate, and comprising:

a support for holding a substrate, a tool for applying a breaking force to an electrically conductive ball deposit on the substrate, a force detector for generating a force output corresponding to the force applied by the tool to the ball deposit while the tool is breaking the ball deposit off of the substrate, a displacement detector for generating a displacement output corresponding to the displacement of said tool with reference to said support while the tool is breaking the ball deposit off of the substrate, a processor adapted utilize said force and displacement outputs to determine the absorption of energy by said ball deposit during breaking, said processor being additionally adapted to determine the portion of energy absorbed by said ball deposit by reference to a peak of transient force detected by said detector, and said processor being still further adapted to indicate a mode of failure by comparing said portion to a reference value.

The load applied to the ball deposit may be via a shear tool or via a pull tool, as previously described.

The energy absorbed by the ball deposit is in one embodiment of approximately the same magnitude for both failure modes up to the point of maximum applied force. It has been observed by the applicant, however, that the energy absorbed after the point of peak applied force may be markedly different. Accordingly, a determination of this post peak applied force portion of absorbed energy can be used to determine the mode of failure by reference to a predetermined energy value. This predetermined energy value can be determined empirically by repetitive tests, taking into consideration the bonding method and size of the ball deposit.

An advantage of the invention is that existing methods of measurement of applied force can be utilized in conjunction with displacement measurement, so as to permit determination of a force/displacement characteristic, and thus determination of a value representing the portion of energy which is absorbed after the point of maximum applied force. This value need not be determined absolutely, but can nevertheless be compared with a suitable reference value to indicate whether failure is by ductile or brittle fracture. The value may also be provided as an absolute value, where required.

It will be appreciated that the comparison may indicate whether the measured value is above or below the reference value, in order to allow an appropriate conclusion to be drawn. A determination that the measured value is above the reference value indicates ductile failure mode whereas a determination that the measured value is below the reference value indicates brittle failure mode, since producing a ductile failure takes more force than producing a brittle failure.

In the case of a plurality of peaks of applied force, the apparatus may be adapted to distinguish said peaks, and eliminate any peak which is considered insignificant by reference to a predetermined standard.

In a refinement, the method and apparatus takes into account speed. Thus tests may be performed at a range of impact speeds of a shear tool upon the stationary ball deposit. The measurements from these tests can be used to determine the mode of failure. For example, it may be shown that for a given bonding method, the frequency of brittle fracture may increase as speed of movement of the tool increases. Brittle failure mode will occur at lower speeds than ductile failure mode. It is desirable to select a value of speed which best distinguishes between brittle and ductile failure.

Several methods may be used to determine an optimum tool speed. The speed should not be so low as to allow the majority of balls to exhibit ductile failure, nor so high as to cause inevitable brittle failure. What is required is a speed which allows all acceptance bonds to exhibit ductile failure, and this speed can for example be determined empirically from an examination of broken bonds.

Preferably the method of the invention includes the step of applying the force at a speed selected to ensure that a satisfactory bond between the ball and component exhibits ductile failure, whereas an unsatisfactory bond exhibits brittle failure.

The apparatus of the invention may further include variable speed means for applying said force to said ball, said variable speed means being selectable in the range 0.5 m/sec. to 10 m/sec.

In a preferred embodiment the apparatus includes an electronic analysis module for receiving digital signals representing changes in applied force and displacement with time, and adapted to integrate and otherwise process such signals to produce values of energy absorbed, peak applied force and rate of change of force, and to process said values to determine a mode of failure, in some embodiments utilizing preset parameters.

BRIEF DESCRIPTION OF THE DRAWINGS

Other features of the invention will be apparent from the following description of a preferred embodiment illustrated by way of example only in conjunction with the accompanying drawings, in which.

DETAILED DESCRIPTION

Figure 1:
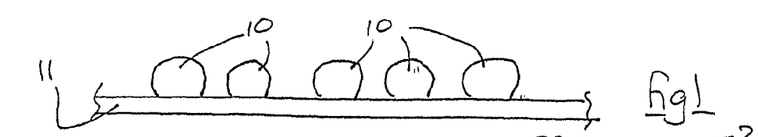
FIG. 1 shows in side elevation an array of solder balls on a substrate.

With reference to the drawings, an array of solder balls 10 is provided on a substrate 11. The balls are typically in the diameter range 0.1-1.0 mm, and closely spaced. The balls may be in a linear array, or may for example be provided on a two-dimensional grid.

Figure 2A:
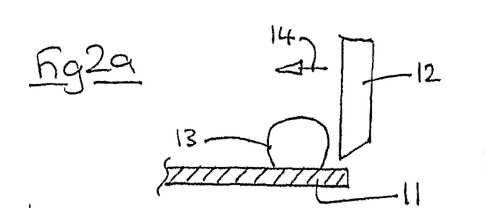
FIG. 2a illustrates schematically a shear test.
Figure 2B:
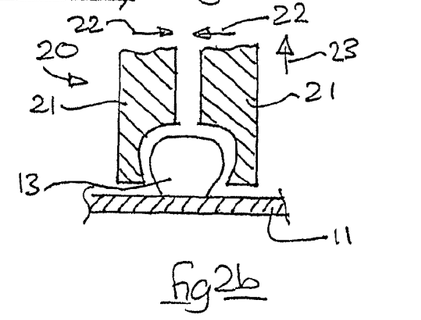
FIG. 2b illustrates schematically a pull test.

Bond strength at the ball/substrate interface may be tested in shear using apparatus illustrated schematically in FIG. 2a. A shear tool 12, which may be shaped to conform to the curved surface of ball 13, is applied to the ball in the direction of arrow 14. Force is gradually increased until the ball shows ductile or brittle failure. Bond strength may be tested in tension using apparatus illustrated schematically in FIG. 2b. A pull tool 20 comprises opposite gripping jaws 21 which may be lowered and closed about a ball deposit 13 in the direction of arrows 22, and then used to exert a pull force in the direction of arrow 23.

Figure 3:
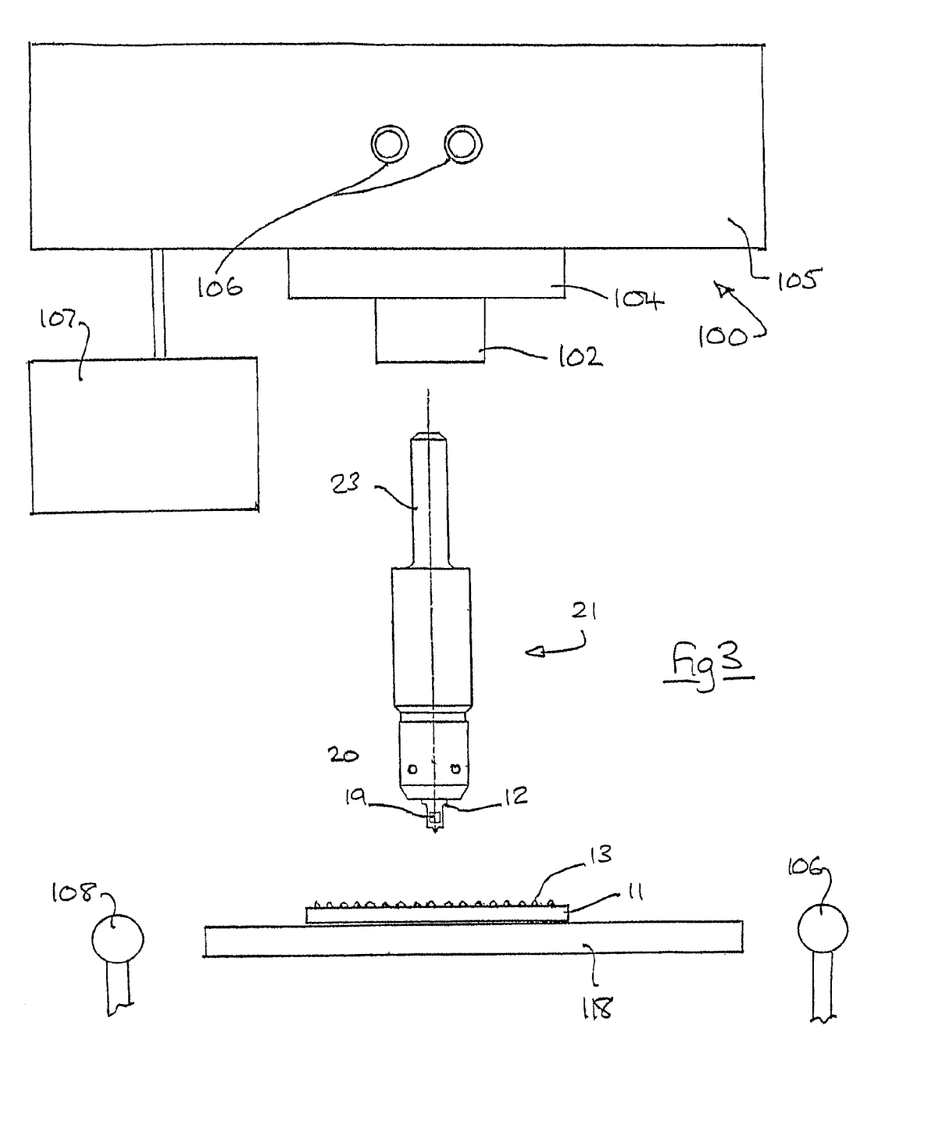
FIG. 3 illustrates schematically a prior art bond testing machine.

FIG. 3 schematically illustrates a known shear testing apparatus which is adapted to sense and record the force required to shear a ball deposit off of a substrate. Such a system typically utilizes strain gauges which produce an electrical output proportionate to the shear force. The commercially available Dage Model 4000 Series machine, previously mentioned, is an example of such a testing apparatus.

In the machine of FIG. 3 the shank 23 of a tool holder 21 which holds a shear tool 12 is secured in a chuck 102 which is in turn mounted on a tool mover 104. Tool mover 104 provides movement in the X direction, for example, of the shear tool 12 to shear a ball deposit 13 off substrate 11 and movement in the Z direction to vertically position the shear tool 12 with respect to the ball deposits 13. Substrate 11 is mounted in table 118 which provides for movement of the substrate in the X and Y directions relative to shear tool 12. Tool mover 104 is secured to a housing 105 upon which is mounted a high-powered microscope 106. Housing 105 can also include the processor which processes the electrical signals received from a force detecting piezo-electric crystal 19 and preferably displays the result of that processing on a display screen 107 which is attached to the housing 105. The machine 100 also includes joystick controls 106, 108 which move the X-Y table 118 and shear tool 12. The operator looks through the high-powered microscope 106 at the area of the substrate 11 of interest and uses the joy sticks 106, 108 to position the shear tool 12 adjacent to the ball deposit 13 to be sheared off of the substrate 11. Once the shear tool 12 is properly positioned with respect to the ball deposit 13, the tool mover 104 moves the tool 12 a desired distance in the X direction, at a desired speed, to shear the ball deposit 13 off the substrate 11. During this shear event, the piezo-electric crystal 19, in this example, experiences forces of tension and compression and produces an electric signal from the crystal 19 which can be correlated to the shear force required to shear the ball deposit 13 off if the substrate 11.

The electric signal produced by the piezo-electric crystal can be conveyed by insulated wires (not shown) to the processor contained within housing 105.

The shear tool 12 travels at a predetermined height above the substrate so as to eliminate dragging forces, and to ensure repeatability.

The machine of FIG. 3 is adapted to a pull test by the use of a suitable gripper tool, and by using the tool mover 104 to move the tool a desired distance in the Z direction, at a desired speed to break the ball deposit from the substrate. Suitable force measuring strain gauges are incorporated in the tool or in the cartridge to which the tool is attached.

Figure 4:
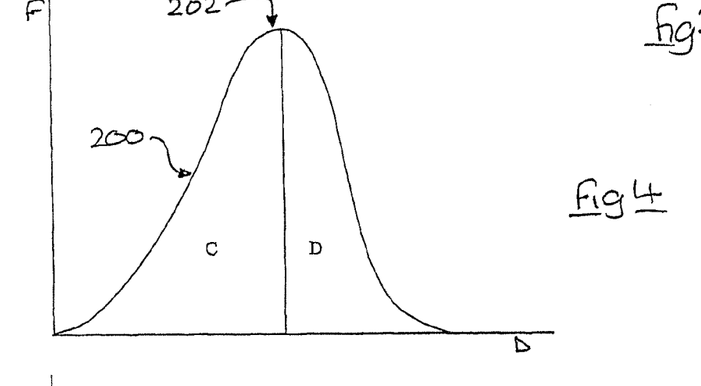
FIG. 4 shows a force/displacement characteristic for brittle failure.
Figure 5:
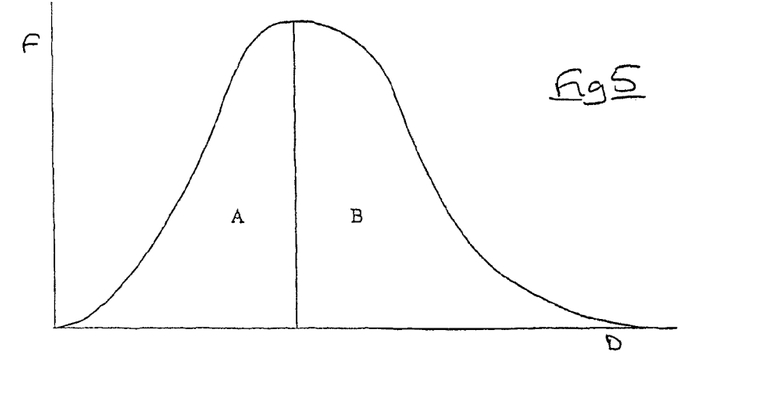
FIG. 5 shows a force/displacement characteristic for ductile failure.

Typical characteristics of ductile and brittle failure are illustrated in FIGS. 4 and 5 by reference to shear tests; similar characteristics are obtained in relation to pull tests. In both FIG. 4 and FIG. 5 the force (F) applied by the tool to the ball deposit is increased along the vertical axis of the graph, displacement (D) of the shear tool occurs along the horizontal axis of the graph as the ball exhibits a combination of elastic (recoverable) deformation and ductile or brittle (unrecoverable) deformation. This combination effect causes a slight curvature to the shape of the graph on the upslope 200, in contrast to the common straight characteristic of pure elastic deformation. The graphs illustrated are somewhat simplified in order to show a smoothed transition as failure occurs.

In both ductile and brittle failure mode, the energy absorbed up to the point 202 of maximum applied force is about the same, as can be seen by a comparison of the areas marked C and A. Energy is a function of force and displacement and therefore can be represented by the area under these curves.

However, after the point 202 of maximum force, as the ball or bond is failing, the energy absorbed is significantly different, as represented by areas marked D and B.

Accordingly, in one embodiment, an electronically determined comparison of these areas D and B can give a qualitative assessment of the mode of failure by reference to a predetermined reference value. The reference value may be determined empirically by performing a series of tests on balls of the same size and bonding method, and noting the mode of failure. The reference value may for example be approximately halfway between the energy values of areas D and B. In this example, area D represents a brittle failure mode and area B represents a ductile failure mode in that more energy is required to produce a ductile failure mode (i.e. to shear a good bond) than a brittle failure mode (i.e. to shear a poor bond).

Any suitable linear displacement means may be used to sense displacement of the tool, and in conjunction with force measurement to permit calculation of the absolute value of energy to failure, if desired. A system such as that shown in FIG. 3 could be used, for example. Force can be measured using strain gauges contained within the cartridge 104, which as previously mentioned, is illustrated in some detail in WO-A-2005/114722.

In this type of system, the servomotors adapted to give relative movement between the tool and substrate in the X-Y direction will produce co-ordinates of the actual tool position. From these co-ordinates, and an internal computer clock, the displacement of the tool, and the speed thereof can be calculated. The test speed may be held constant by a closed loop servo system close to the programmed speed. The actual test speed (correcting for slight differences between the programmed speed and the real speed) is measured from servo position sensors and time data. The force time data is transformed to force distance by the product of the time data and the actual test speed in a known manner.

These force and displacement measurements would be used to generate the curves of FIGS. 4 and 5. Once these curves have been plotted, readily available, or easily written, software algorithms could be used to calculate the areas B and D and to compare those areas to an empirically determined reference value. The software could be contained in, for example, a computer (not shown) contained within the housing 105 of FIG. 3. The computer could then produce an output displayed on monitor 107 to indicate to the user whether the shear test indicated a ductile failure mode or brittle failure mode. This information would indicate to the user whether a shear test indicated good bond strength (ductile failure mode) or poor bond strength (brittle failure mode) for the bond being tested.

The accuracy of this calculation is a function of the measurement repeat rate. Thus for example an adequate repeat rate may give 20 measurements of force in calculating the area C. Each measurement could be at a pre-set increment of displacement.

A less frequent repeat rate may be sufficient where the threshold between areas D & B is easily detected. In contrast, a more frequent rate may be selected in a relatively fine threshold, where closely adjacent measurements of force are required to identify the position of the peak force with sufficient precision.

In a refinement of the invention, the tool 12 is applied to the ball at a variety of impact speeds to determine the robustness of the bonding method, and particularly to demonstrate that at the appropriate impact speed all good bonds exhibit ductile failure, or conversely that all bad bonds exhibit brittle failure.

In a further refinement of the invention, the areas A-D may be individually calculated and compared in order to demonstrate a sequence of failure modes. Thus FIG. 6 shows an ascending level of energy values corresponding to pre-selected threshold appropriate to each portion A-D of the graphs of FIGS. 4 and 5.

Figure 6:
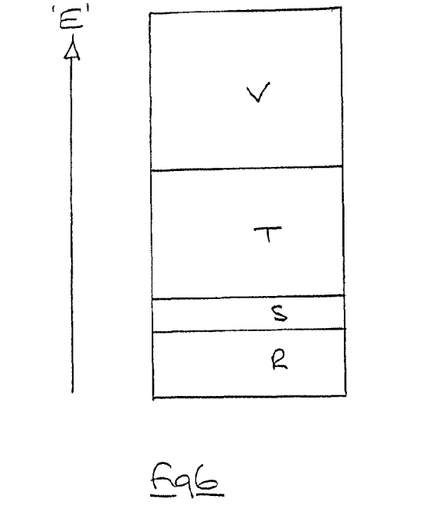
FIG. 6 shows a bar chart comparison of energy thresholds.

In FIG. 6 increasing post peak energy is represented by the arrow 'E' and four failure modes R, S, T and V are represented by the horizontal dimensions. Thus the division between R and S represents the energy value at which a failure mode changes from mode R to mode S, and so on.

Figure 6A:
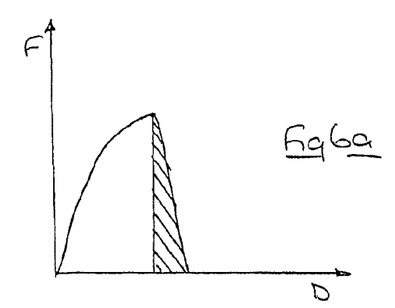
FIGS. 6a-6d indicate force/displacement characteristics representative of modes of failure indicated by the energy values of FIG. 6.

FIG. 6a represents failure mode R where post-peak energy is equivalent to the shaded portion.

Figure 6B:
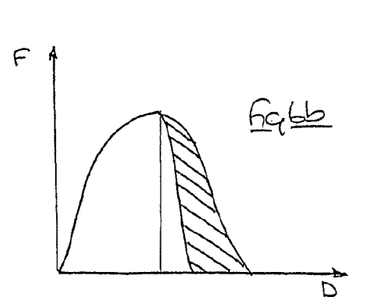

FIG. 6b represents a different mode of failure S where post-peak energy is equivalent to the shaded portion.

Figure 6C:
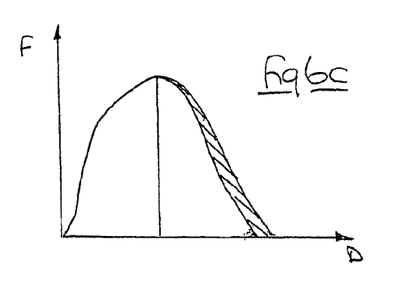
Figure 6D:
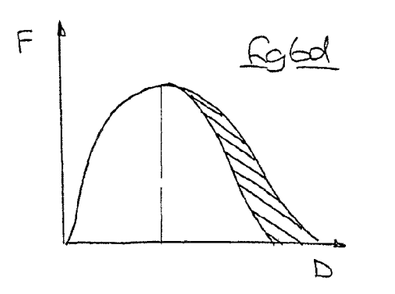

FIG. 6c and FIG. 6d represent the further respective modes of failure T, V having successively greater post-peak energies.

In a chart of the kind represented by FIG. 6, the horizontal divisions (energy thresholds) may be refined according to other measurable features of the particular failure mode.

Figure 7:
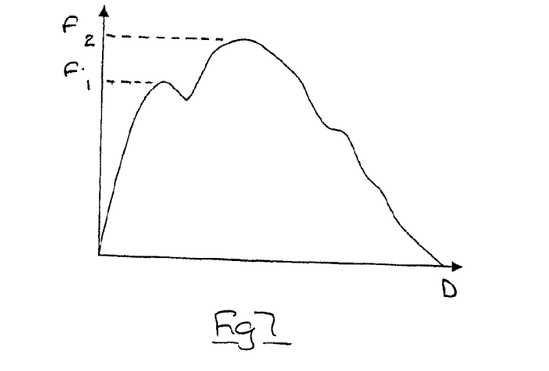
FIG. 7 shows a force/displacement characteristic for pad cratering failure.

FIG. 7 illustrates an actual force-displacement curve of the general form illustrated in FIG. 5. FIG. 7 however indicates a so-called pad-cratering failure which has a successive peak forces $F_1$ and $F_2$ on the up-slope. The term "pad cratering failure" means a failure in which the electrically conductive pad to which the ball deposit is adhered lifts from the substrate taking a portion of the substrate with it leaving a corresponding crater in the aforementioned substrate. A pad-cratering failure is one specific mode of failure into which test results might be desirably categorized. To detect this failure, the software algorithm utilized by the computer would monitor the shear tool force sensors to look for a first lower peak F1 followed by a second higher peak F2. If this condition is detected, the computer would output a message on monitor 107 indicating a pad cratering failure to the user. This information would be useful to the user because it indicates what parts of the bond construction are the weakest, be it ductile, brittle or pad crater.

Figure 8A:
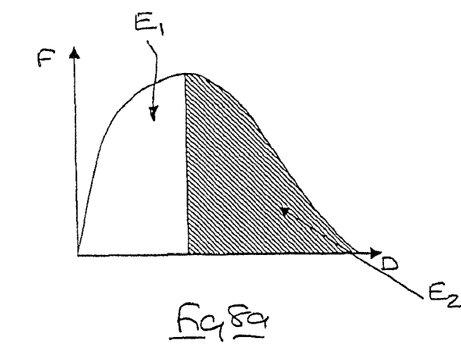
FIGS. 8-8d show comparative force/displacement characteristics of ductile and pad cratering failure.

FIG. 8a illustrates a conventional ductile failure with post-peak energy $E_2$ being somewhat greater than pre-peak energy $E_1$. FIG. 8a has a single clearly identifiable peak energy.

Figure 8B:
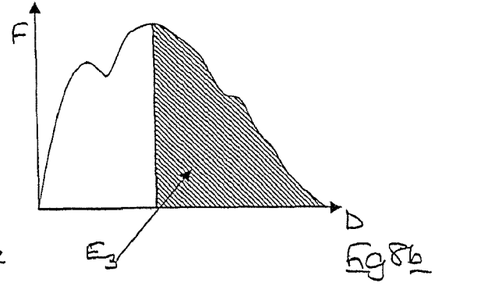

FIG. 8b shows the pad-cratering failure of FIG. 7 in which the second (maximum) peak is identified as the dividing point. In this analysis post-peak energy $E_3$ is rather similar to the post-peak energy $E_2$ of FIG. 8a.

Figure 8C:
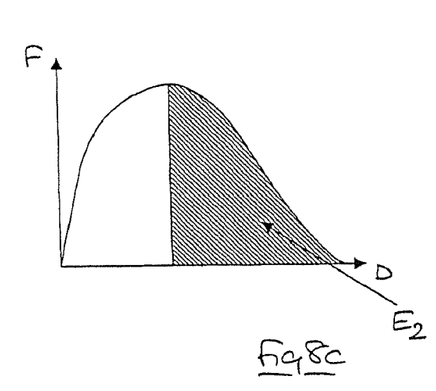
Figure 8D:
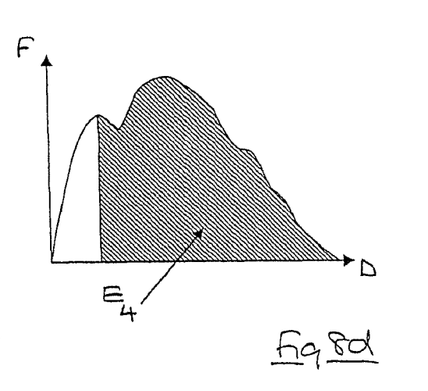

In contrast FIGS. 8c and 8d show the same graphs as FIGS. 8a and 8b, but the dividing point is determined by the first peak of the pad-cratering example. Clearly in this case the post peak energy $E_4$ is much greater than $E_2$.

Thus in the case that two peaks are detected on the up stage (i.e. a second peak higher than a first peak), such a failure mode could be classified, and a corresponding mode established by comparison of energy subsequent to the first peak. In this example the mode is identified as pad-cratering. It will be understood that each actual test graph may exhibit particular characteristics of for example peak values, peak values in a particular recognizable order, slopes before, after and between peak values, and so on. These values of these parameters can be determined, for example, by digital recording, and selected as required in order to characterize particular failure modes. Thus other failure modes may be indicated by for example three or four peaks. A logical machine analysis may sort or pre-sort the failure data according to particular parameters, so that a two peak signal is analyzed from the second peak, whereas a three peak signal is analyzed from the middle peak.

For each analysis it is recognized that a certain value of 'noise' may be present and/or that the measured values have an accuracy determined by the sophistication of given measuring equipment. Suitable filters, preferably digital electronic filters, may be included to allow predetermined reference values and peaks to be appropriately compared.

Figure 9A:
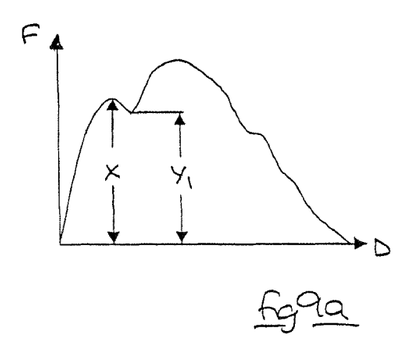
FIGS. 9a-9b show similar but distinguishable force/displacement characteristics of pad cratering failure.
Figure 9B:
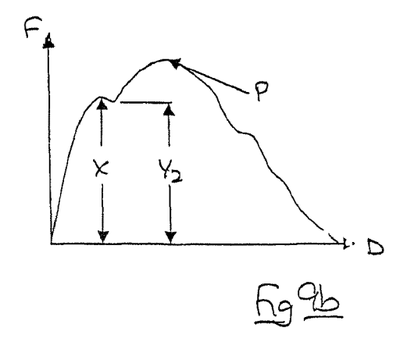

As indicated in FIGS. 9a and 9b, two similar graphs may be distinguished if the successive peaks are separated by a minimum value which is less than a predetermined fraction of the first peak value. Thus in FIG. 9a, the value $Y_2$ is greater than the corresponding value $Y_1$ of FIG. 9a, compared with the first peak value X. In this example FIG. 9a could be treated as a two-peak graph, whereas FIG. 9b could be treated as a single peak graph (indicated by P). Variations are of course possible, and it is envisaged that programmable options may be offered with, for example, the threshold values of $Y_1$, $Y_2$ being settable in order to allow for variations in the kind of ball deposits under test.

As indicated above, a comparison of total energy values may be supplemented by reference to additional factors such as peak energy value. Thus peaks within a settable range may be selected for analysis, whereas peaks outside this range may be excluded.

Energy and peak force value may be used together as a filter of failure modes, in any suitable combination, along with pre and post peak slope values.

Another alternative embodiment, where relative values and/or dimensionless ratios. One dimensionless ratio which is suitable is the numerical ratio of pre and post peak energy such as C:D of FIG. 4, or A:B of FIG. 5. This ratio could be used to indicate a ductile versus brittle failure mode. Likewise force values $F_1:F_2$ of FIG. 7 may be used to indicate a pad crater failure mode.

The force/displacement characteristics illustrated in the accompanying drawings relate specifically to shear tests using apparatus of the general kind illustrated in FIG. 2a. Similar characteristics are obtained from pull test apparatus of the general kind illustrated in FIG. 2b, and allow failure mode to be classified in the same manner, particularly by reference to port-peak energy levels.

It is intended to be understood that this invention is not limited to the embodiments described herein and that variants, obvious to those skilled in the art, can be made which are within the spirit of the invention and scope of the apparatus and method claims appended hereto.

The invention claimed is:

1. A method of determining the mode of bond failure of an electrically conductive ball deposit on a substrate which is subjected to a breaking force by a tool to break at least a part of the ball deposit off the substrate, the method comprising the steps of:
   producing electrical force signals which indicate the force on the tool while the tool is breaking at least a part of the ball deposit off the substrate,
   producing electrical tool displacement signals which indicate the displacement of the tool relative to the substrate while the tool is breaking at least a part of the ball deposit off the substrate;
   processing the electrical force signals to determine a selected peak breaking force,
   utilizing the electrical force signals and electrical tool displacement signals to determine a first value of energy occurring before said selected peak breaking force, and
   utilizing the electrical force signals and electrical tool displacement signals to determine a second value of energy occurring after said selected peak breaking force.

2. A method according to claim 1 wherein said first and second values of energy each correspond to energy absorbed by the ball deposit.

3. A method according to claim 1 wherein said selected peak is determined to be the maximum applied force.

4. A method according to claim 3 wherein said selected peak is determined to be the sole peak.

5. A method according to claim 3 wherein processing the electrical signals further comprises determining a plurality of peaks of breaking force, and the method includes the step of discarding one or more peaks of lower significance.

6. A method according to claim 5 wherein a peak is discarded if the next succeeding minimum has a value greater than a predetermined percentage of the value of that peak.

7. Shear testing apparatus for applying a shear force to an electrically conductive ball deposit on a substrate to shear at least a part of the ball deposit off the substrate, comprising:
   a support for holding the substrate,
   a shear tool mounted to said test apparatus for applying a shear force to the electrically conductive ball deposit on the substrate,
   a force monitoring detector for generating electrical force signals representative of the force applied by the shear tool to the ball deposit during at least a part of the time that the shear tool is shearing at least a part of the ball deposit off of the substrate,
   a displacement monitoring detector for generating electrical displacement signals representative of the displacement of said shear tool by reference to said support during at least a part of the time that the shear tool is shearing at least a part of the ball deposit off of the substrate,
   a computer processor adapted to receive said force signals and displacement signals and to utilize said force signals and displacement signals to determine a value of energy occurring during at least a part of the time that at least a part of said ball is being sheared from said substrate by said shear tool,
   said computer processor further being adapted to utilize said force signals to determine a peak force value,
   said computer processor still further being adapted to determine a portion of the energy value occurring before or after said peak force value.

8. Apparatus according to claim 7 and further including a filter adapted to eliminate one or more peaks of transient force which are of less than predetermined significance.

9. Apparatus according to claim 8, further comprising a user interface operatively connected with the computer processor and adapted for selection of one of a plurality of said peaks of transient force.

10. Apparatus according to claim 7, further comprising a user interface operatively connected with the computer processor and adapted for selection of said portion.

11. Pull testing apparatus for applying a pull force to an electrically conductive ball deposit on a substrate to break at least a part of the ball deposit off the substrate, comprising:
   a support for holding the substrate,
   a pull tool mounted within said test apparatus for applying a pull force to the electrically conductive ball deposit on the substrate,
   a force monitoring detector for generating electrical force signals representative of the force applied by the pull tool to the ball deposit during at least a part of the time that the pull tool is breaking at least a part of the ball deposit off of the substrate,
   a displacement monitoring detector for generating electrical displacement signals representative of the displacement of said pull tool by reference to said support during at least a part of the time that the pull tool is breaking at least a part of the ball deposit off of the substrate,
   a computer processor adapted to receive said force signals and displacement signals and to utilize said force signals and displacement signals to determine an energy value,
   said computer processor furthered being adapted to utilize said force signals to determine a peak force value,
   said computer processor still further being adapted to determine a portion of the energy value occurring before or after said peak force value.

12. Apparatus according to claim 11 and further including a filter adapted to eliminate one or more peaks of transient force which are of less than predetermined significance.

13. Apparatus according to claim 12 further comprising a user interface operatively connected with the computer processor and adapted for selection of one of a plurality of said peaks of transient force.

14. Apparatus according to claim 11, further comprising a user interface operatively connected with the computer processor and adapted for selection of said portion.

* * * * *